United States Patent
Gross

(10) Patent No.: US 11,413,455 B1
(45) Date of Patent: Aug. 16, 2022

(54) ELECTRICAL TREATMENT OF ALZHEIMER'S DISEASE

(71) Applicant: RAINBOW MEDICAL LTD., Herzliya (IL)

(72) Inventor: Yossi Gross, Moshav Mazor (IL)

(73) Assignee: RAINBOW MEDICAL LTD., Herzliya (IL)

( * ) Notice: Subject to any disclaimer, the term of this patent is extended or adjusted under 35 U.S.C. 154(b) by 0 days.

(21) Appl. No.: 17/667,051

(22) Filed: Feb. 8, 2022

(51) Int. Cl.
| | |
|---|---|
| *A61N 1/36* | (2006.01) |
| *A61N 1/20* | (2006.01) |
| *A61N 1/04* | (2006.01) |

(52) U.S. Cl.
CPC ....... *A61N 1/36025* (2013.01); *A61N 1/0456* (2013.01); *A61N 1/20* (2013.01); *A61N 1/36034* (2017.08)

(58) Field of Classification Search
CPC .... A61N 1/36025; A61N 1/0456; A61N 1/20; A61N 1/36034
See application file for complete search history.

(56) References Cited

U.S. PATENT DOCUMENTS

| | | |
|---|---|---|
| 4,044,774 A | 8/1977 | Corbin et al. |
| 4,503,863 A | 3/1985 | Katims |
| 4,602,638 A | 7/1986 | Adams |
| 4,738,250 A | 4/1988 | Fulkerson et al. |
| 5,088,977 A | 2/1992 | Sibalis |
| 5,121,754 A | 6/1992 | Mullett |
| 5,433,739 A | 7/1995 | Sluijter et al. |
| 5,529,574 A | 6/1996 | Frackelton |
| 5,792,100 A | 8/1998 | Shantha |
| 5,911,223 A | 6/1999 | Weaver et al. |

(Continued)

FOREIGN PATENT DOCUMENTS

| | | |
|---|---|---|
| JP | 2004-321242 | 11/2004 |
| JP | 2005/011805 | 2/2005 |

(Continued)

OTHER PUBLICATIONS

Karran September E et201 al., 1 "The Amyloid cascade hypothesis for AD," Nature Reviews Drug Discovery, vol. 10; 698-712.

(Continued)

*Primary Examiner* — Amanda K Hulbert
*Assistant Examiner* — Philip C Edwards
(74) *Attorney, Agent, or Firm* — Sughrue Mion, PLLC

(57) ABSTRACT

A method is provided including disposing central electrodes outside and in electrical contact with a skull of a head of a subject identified as at risk of or suffering from Alzheimer's disease, within one cm of a sagittal midplane of the skull; and disposing peripheral electrodes outside and in electrical contact with the skull, superior to an orbitomeatal plane of the skull and inferior to a first plane midway between the orbitomeatal plane and a cranial vertex of the skull, the first plane parallel to the orbitomeatal plane. The subject is treated by clearing amyloid beta, tau protein, and/or metal ions from brain parenchyma to a subarachnoid space, by activating control circuitry to apply respective currents between one or more of the central electrodes and two or more of the peripheral electrodes, and configure the central electrodes as cathodes and the peripheral electrodes as anodes. Other embodiments are also described.

32 Claims, 3 Drawing Sheets

(56) References Cited

U.S. PATENT DOCUMENTS

| | | | |
|---|---|---|---|
| 5,938,690 A | 8/1999 | Law et al. |
| 6,041,252 A | 3/2000 | Walker et al. |
| 6,146,380 A | 11/2000 | Racz et al. |
| 6,161,047 A | 12/2000 | King et al. |
| 6,360,750 B1 | 3/2002 | Gerber et al. |
| 6,567,702 B1 | 5/2003 | Nekhendzy et al. |
| 6,591,138 B1 | 7/2003 | Fischell et al. |
| 6,602,248 B1 | 8/2003 | Sharps et al. |
| 6,620,155 B2 | 9/2003 | Underwood et al. |
| 6,941,172 B2 | 9/2005 | Nachum |
| 6,997,941 B2 | 2/2006 | Sharkey et al. |
| 7,013,177 B1 | 3/2006 | Whitehurst et al. |
| 7,120,489 B2 | 10/2006 | Shalev et al. |
| 7,155,287 B2 | 12/2006 | Gavronsky |
| 7,217,351 B2 | 5/2007 | Krumme |
| 7,223,227 B2 | 5/2007 | Pflueger |
| 7,270,659 B2 | 9/2007 | Ricart et al. |
| 7,317,947 B2 | 1/2008 | Wahlstrand et al. |
| 7,398,121 B2 | 7/2008 | Matsumura et al. |
| 7,509,171 B2 | 3/2009 | DiMauro |
| 7,640,062 B2 | 12/2009 | Shalev |
| 7,818,063 B2 | 10/2010 | Wallace et al. |
| 7,831,306 B2 | 11/2010 | Finch et al. |
| 7,860,569 B2 | 12/2010 | Solberg et al. |
| 8,060,207 B2 | 11/2011 | Wallace et al. |
| 8,190,248 B2 | 5/2012 | Besio et al. |
| 8,353,853 B1 | 1/2013 | Kyle et al. |
| 8,457,761 B2 | 6/2013 | Wariar |
| 8,577,469 B2 | 11/2013 | Gross |
| 8,676,348 B2 | 3/2014 | Gross |
| 8,731,674 B2 | 5/2014 | Wallace et al. |
| 9,616,221 B2 | 4/2017 | Gross |
| 9,724,513 B2 | 8/2017 | Lane et al. |
| 9,724,515 B2 | 8/2017 | Fostick et al. |
| 9,731,122 B2 | 8/2017 | Gross |
| 10,173,063 B2 | 1/2019 | Fostick et al. |
| 10,398,884 B2 | 9/2019 | Lad et al. |
| 10,569,086 B2 | 2/2020 | Fostick et al. |
| 10,881,858 B1* | 1/2021 | Gross .................. A61N 1/0504 |
| 10,898,716 B2 | 1/2021 | Fostick et al. |
| 2002/0151948 A1 | 10/2002 | King et al. |
| 2002/0183683 A1 | 12/2002 | Lerner |
| 2003/0130707 A1 | 7/2003 | Gan et al. |
| 2003/0158589 A1 | 8/2003 | Katsnelson |
| 2003/0216792 A1 | 11/2003 | Levin et al. |
| 2003/0225331 A1 | 12/2003 | Diederich et al. |
| 2004/0002746 A1 | 1/2004 | Ryan et al. |
| 2004/0019381 A1 | 1/2004 | Pflueger |
| 2004/0049180 A1 | 3/2004 | Sharps et al. |
| 2004/0116977 A1 | 6/2004 | Finch et al. |
| 2004/0210209 A1 | 10/2004 | Yeung et al. |
| 2005/0010205 A1 | 1/2005 | Hovda et al. |
| 2005/0021104 A1 | 1/2005 | DiLorenzo |
| 2005/0119650 A1 | 6/2005 | Sanders et al. |
| 2005/0137646 A1 | 6/2005 | Wallace et al. |
| 2005/0137647 A1 | 6/2005 | Wallace et al. |
| 2005/0159790 A1 | 7/2005 | Shalev |
| 2005/0187589 A1 | 8/2005 | Wallace et al. |
| 2005/0203599 A1 | 9/2005 | Garabedian et al. |
| 2005/0203600 A1 | 9/2005 | Wallace et al. |
| 2005/0203602 A1 | 9/2005 | Wallace et al. |
| 2005/0222647 A1 | 10/2005 | Wahlstrand et al. |
| 2005/0277996 A1 | 12/2005 | Podhajsky et al. |
| 2006/0030895 A1 | 2/2006 | Simon et al. |
| 2006/0106430 A1 | 5/2006 | Fowler et al. |
| 2006/0224223 A1 | 10/2006 | Podhajsky et al. |
| 2006/0293723 A1 | 12/2006 | Whitehurst et al. |
| 2007/0000784 A1 | 1/2007 | Paul et al. |
| 2007/0073402 A1 | 3/2007 | Vresilovic et al. |
| 2007/0162086 A1 | 7/2007 | Dilorenzo |
| 2007/0213700 A1 | 9/2007 | Davison et al. |
| 2007/0255338 A1 | 11/2007 | Wahlstrand |
| 2008/0009927 A1 | 1/2008 | Vilims |
| 2008/0119907 A1 | 5/2008 | Stahmann |
| 2008/0260542 A1 | 10/2008 | Nishikawa et al. |
| 2009/0062885 A1 | 3/2009 | Brighton et al. |
| 2009/0112278 A1 | 4/2009 | Wingeier et al. |
| 2009/0125080 A1 | 5/2009 | Montgomery |
| 2009/0126813 A1 | 5/2009 | Yanagisawa et al. |
| 2009/0131850 A1 | 5/2009 | Geiger |
| 2009/0312816 A1 | 12/2009 | Gross |
| 2010/0217369 A1 | 8/2010 | Gross |
| 2010/0324441 A1 | 12/2010 | Hargrove et al. |
| 2011/0046540 A1 | 2/2011 | Alterman et al. |
| 2011/0054518 A1 | 3/2011 | Carbunaru et al. |
| 2011/0160638 A1 | 6/2011 | Mauge et al. |
| 2011/0160797 A1 | 6/2011 | Makous et al. |
| 2012/0053659 A1 | 3/2012 | Molnar et al. |
| 2012/0191159 A1 | 7/2012 | Willeford |
| 2012/0203307 A1 | 8/2012 | Schroeppel et al. |
| 2013/0066392 A1 | 3/2013 | Simon et al. |
| 2013/0102952 A1 | 4/2013 | Gross |
| 2013/0166006 A1 | 6/2013 | Williams |
| 2013/0289385 A1 | 10/2013 | Lozano et al. |
| 2014/0058189 A1 | 2/2014 | Stubbeman |
| 2014/0088672 A1 | 3/2014 | Bedenbaugh |
| 2014/0207224 A1 | 7/2014 | Simon |
| 2014/0257168 A1 | 9/2014 | Gill |
| 2014/0324128 A1 | 10/2014 | Gross |
| 2015/0011927 A1 | 1/2015 | Hua |
| 2015/0038948 A1* | 2/2015 | Ludvig .................. A61B 5/375 |
| | | 604/891.1 |
| 2015/0119898 A1 | 4/2015 | Desalles et al. |
| 2016/0144164 A1 | 5/2016 | Sedighiani |
| 2016/0331970 A1 | 11/2016 | Lozano |
| 2017/0007823 A1 | 1/2017 | Gross |
| 2017/0056642 A1 | 3/2017 | Moffitt et al. |
| 2017/0120053 A1 | 5/2017 | Fostick et al. |
| 2017/0182317 A1 | 6/2017 | Gross et al. |
| 2017/0296821 A1 | 10/2017 | Fostick et al. |
| 2018/0071523 A1 | 3/2018 | Gross et al. |
| 2018/0193646 A1* | 7/2018 | Fostick .................. A61N 1/20 |
| 2018/0318575 A1 | 11/2018 | Gross et al. |
| 2019/0076653 A1* | 3/2019 | Fostick ................ A61N 1/0529 |
| 2019/0282807 A1* | 9/2019 | Tendler .................. A61N 1/327 |

FOREIGN PATENT DOCUMENTS

| | | |
|---|---|---|
| JP | 2007-501067 | 1/2007 |
| WO | 94/05369 | 3/1994 |
| WO | 01/52931 | 7/2001 |
| WO | 01/85027 | 11/2001 |
| WO | 2001/085094 | 11/2001 |
| WO | 2006/090397 | 8/2006 |
| WO | 2008/007369 | 1/2008 |
| WO | 2017/006327 | 1/2017 |
| WO | 2017/072769 | 5/2017 |
| WO | 2017/115351 | 7/2017 |
| WO | 2018/051338 | 3/2018 |

OTHER PUBLICATIONS

De La Torre JC, "Vascular Basis of Alzheimer's Pathogensis," Ann NY Acad Sci. 977:196-215 (Nov. 2002).

Weller RO et al, "Perivascular Drainage of Amyloid-b Peptides from the Brain and Its Failure in Cerebral Amyloid Angiopathy and Alzheimer's Disease," Brain Pathology 18 (Apr. 2008) 253-266.

Brief PubMed search for metal ions in Alzheimers.

An Office Action dated Sep. 27, 2016, which issued during the prosecution of U.S. Appl. No. 14/926,705.

An International Search Report and a Written Opinion both dated Aug. 7, 2008, which issued during the prosecution of Applicant's PCT/IL2007/000865.

An Office Action dated Mar. 29, 2013, which issued during the prosecution of U.S. Appl. No. 12/373,306.

An Office Action dated Oct. 31, 2011, which issued during the prosecution of U.S. Appl. No. 12/373,306.

An Office Action dated Oct. 1, 2012, which issued during the prosecution of U.S. Appl. No. 12/373,306.

Notice of Allowance dated Jul. 24, 2013, which issued during the prosecution of U.S. Appl. No. 12/373,306.

(56) References Cited

OTHER PUBLICATIONS

An Office Action dated Apr. 11, 2013, which issued during the prosecution of U.S. Appl. No. 13/663,757.
Notice of Allowance dated Oct. 28, 2013, which issued during the prosecution of U.S. Appl. No. 13/663,757.
Elixmann IM et al., "In-vitro evaluation of a drainage catheter with integrated bioimpedance electrodes to determine ventricular size," Biomed Tech 2013; 58 (Suppl. 1) Sep. 2013 (2 pages total).
An Office Action dated Aug. 31, 2015, which issued during the prosecution of U.S. Appl. No. 13/872,794.
An Applicant Initiated Interview Summary dated Dec. 14, 2015, which issued during the prosecution of U.S. Appl. No. 13/872,794.
An Office Action dated Feb. 3, 2016, which issued during the prosecution of U.S. Appl. No. 13/872,794.
Notice of Allowance dated Dec. 9, 2016, which issued during the prosecution of U.S. Appl. No. 14/794,739.
An Applicant Initiated Interview Summary dated Feb. 25, 2016, which issued during the prosecution of U.S. Appl. No. 13/872,794.
An Office Action dated Jun. 15, 2016, which issued during the prosecution of U.S. Appl. No. 13/872,794.
An International Search Report and a Written Opinion both dated Oct. 20, 2016, which issued during the prosecution of Applicant's PCT/IL2016/050728.
An Office Action dated Sep. 21, 2016, which issued during the prosecution of U.S. Appl. No. 14/794,739.
An International Search Report and a Written Opinion both dated Jan. 26, 2017, which issued during the prosecution of Applicant's PCT/IL2016/051161.
Notice of Allowance dated Jul. 14, 2017, which issued during the prosecution of U.S. Appl. No. 13/872,794.
An Office Action dated May 26, 2017, which issued during the prosecution of U.S. Appl. No. 15/453,290.
An International Preliminary Report on Patentability dated Apr. 7, 2009, which issued during the prosecution of Applicant's PCT/IL2007/000865.
Loutzenhiser, "Membrane Potential measurements in renal afferent and efferent arterioles: actions of Angiotensin II", AJP—Renal Physiol Aug. 1, 1997 vol. 273 No. 2 F307-F314.
U.S. Appl. No. 60/830,717, filed Jul. 12, 2006.
Dao-Sheng Liu et al., "Activation of Na+ and K+ Pumping Modes of (Na,K)-ATPase by an Oscillating Electric Field," the Journal of Biological Chemistry, vol. 265. No. 13, May 5, 1990. (pp. 7260-7267).
Robert F. Service.. "Electric fields deliver drugs into tumors." http://news.sciencemaa.ora. Feb. 4, 2015. (5 Pages Total).
Vernengo J, "Injectable Bioadhesive Hydrogels for Nucleus Pulposus Replacement and Repair of the Damaged Intervertebral Disc: A Thesis," Drexel University (Jan. 2007).
Urban JPG et al., "The nucleus of the intervertebral disc from development to degeneration," American Zoologist 40(1): 53-61 (2000).
Cheung KMC et al., "Intervertebral disc regeneration by use of autologous mesenchymal stem cells, an experimental model in rabbits," Abstract from the SRS 2004 Annual Meeting.
Freemont TJ et al., "Degeneration of intervertebral discs: current understanding of cellular and molecular events, and implications for novel therapies," Expert Reviews in Molecular Biology, Mar. 29, 2001 (Cambridge University Press).
An Office Action dated Sep. 12, 2011, which issued during the prosecution of U.S. Appl. No. 12/373,306.
An Office Action dated Jul. 24, 2017, which issued during the prosecution of U.S. Appl. No. 14/982,187.

An International Search Report and a Written Opinion both dated Mar. 10, 2017, which issued during the prosecution of Applicant's PCT/IL2016/051363.
An Office Action dated Apr. 25, 2018, which issued during the prosecution of U.S. Appl. No. 15/637,330.
U.S. Appl. No. 62/444,939, filed Jan. 11, 2017.
An Office Action dated Nov. 29, 2019, which issued during the prosecution of U.S. Appl. No. 15/969,411.
Sawyer, P N et al. "Measurement of streaming potentials of mammalian blood vessels, aorta and vena cava, in vivo." Biophysical journal vol. 6,5 (1966): 641-51. doi:10.1016/50006-3495(66)86683-3, https://www.ncbi.nlm.nih.gov/pmc/articles/PMC1368020/, viewed on Jul. 22, 2019.
An Office Action dated Jul. 29, 2019, which issued during the prosecution of U.S. Appl. No. 15/618,325.
An International Search Report and a Written Opinion both dated May 23, 2019, which issued during the prosecution of Applicant's PCT/IL2019/050284.
An Office Action dated Jul. 10, 2019, which issued during the prosecution of U.S. Appl. No. 15/864,065.
Notice of Allowance dated Oct. 17, 2019, which issued during the prosecution of U.S. Appl. No. 15/864,065.
An Office Action dated Mar. 25, 2019, which issued during the prosecution of U.S. Appl. No. 15/742,245.
Austin SA et al., "Mechanisms of microglial activation by amyloid precursor protein and its proteolytic fragments "In Lane TE et al. (eds.), Central nervous system diseases and inflammation. Springer US, New York, pp. 13-32 (2008).
Farfara D et al., "γ-Secretase component presenilin is important for microglia β-amyloid clearance," Ann Neurol. Jan. 2011;69(1):170-80.
Kearns KR et al., "Macrophage response to electrical stimulation," in 2015 41st Annual Northeast Biomedical Engineering Conference (NEBEC), Apr. 2015.
Nagele RG et al., "Contribution of glial cells to the development of amyloid plaques in Alzheimer's disease" (Abstract only), Neurobiol Aging. May-Jun. 2004;25(5):663-74.
"The role of glial cells in amyloid-beta clearance," Abstract, Vumc (Amsterdam, the Netherlands) Feb. 20, 2016.
Iaccarino HF et al., "Gamma frequency entrainment attenuates amyloid load and modifies microglia," Nature, 540:230-251, Dec. 2016.
Devlin H, "Strobe lighting provides a flicker of hope in the fight against Alzheimer's," The Guardian, Dec. 7, 2016.
An Office Action dated Mar. 6, 2020, which issued during the prosecution of U.S. Appl. No. 15/618,325.
An Office Action together with the English translation dated Aug. 19, 2020, which issued during the prosecution of Japanese Patent Application No. 2018-521586.
An Office Action dated Mar. 30, 2020, which issued during the prosecution of U.S. Appl. No. 16/574,772.
An Office Action dated Nov. 20, 2020, which issued during the prosecution of U.S. Appl. No. 16/353,407.
An International Search Report and a Written Opinion both dated Dec. 20, 2020, which issued during the prosecution of Applicant's PCT/IL2020/051022.
An Office Action dated May 25, 2021, which issued during the prosecution of U.S. Appl. No. 16/353,407.
An Office Action dated Nov. 4, 2021, which issued during the prosecution of U.S. Appl. No. 16/713,660.
Final Office Action issued in U.S. Appl. No. 16/353,407, dated May 25, 2021.
Non-Final Office Action issued in U.S. Appl. No. 17/402,911, dated Oct. 28, 2021.

* cited by examiner

ELECTRICAL TREATMENT OF ALZHEIMER'S DISEASE

FIELD OF THE APPLICATION

The present invention relates generally to treatment and prevention of Alzheimer's diseases, and specifically to electrical techniques for treating and preventing Alzheimer's disease.

BACKGROUND OF THE APPLICATION

Alzheimer's disease is a chronic neurodegenerative disease that causes dementia. Accumulation of amyloid beta in the brain is widely believed to contribute to the development of Alzheimer's disease.

US Patent Application Publication 2014/0324128 to Gross, which is incorporated herein by reference, describes apparatus for driving fluid between first and second anatomical sites of a subject. The apparatus comprises (1) a first electrode, configured to be coupled to the first anatomical site of the subject; (2) a second electrode, configured to be coupled to the second anatomical site of the subject; and (3) a control unit, configured to (i) detect a pressure difference between the first and second anatomical sites, and (ii) in response to the detected pressure difference, drive fluid between the first and second anatomical sites by applying a treatment voltage between the first and second electrodes. Other embodiments are also described.

PCT Publication WO 2017/006327 to Gross, which is incorporated herein by reference, describes an electrical amyloid beta-clearance system for treating a subject identified as at risk of or suffering from Alzheimer's disease. The system includes (a) midplane treatment electrodes, adapted to be disposed over a superior sagittal sinus, outside and in electrical contact with a skull of a head of the subject; and (b) lateral treatment electrodes, adapted to be disposed between 1 and 12 cm of a sagittal midplane of the skull. The system further includes control circuitry, configured to clear amyloid beta from a subarachnoid space to the superior sagittal sinus, by applying one or more treatment currents between (a) one or more of the midplane treatment electrodes and (b) one or more of the lateral treatment electrodes. Other embodiments are also described.

PCT Publication WO 2017/072769 to Fostick et al., which is incorporated herein by reference, describes a system that includes a parenchymal electrode, configured to be implanted in brain parenchyma of a subject identified as at risk of or suffering from a disease; and a cerebrospinal fluid (CSF) electrode, configured to be implanted in a CSF-filled space of a brain of the subject, the CSF-filled space selected from the group consisting of: a ventricular system and a subarachnoid space. Control circuitry is configured to drive the parenchymal electrode and the CSF electrode to clear a substance from the brain parenchyma into the CSF-filled space of the brain. Other embodiments are also described.

SUMMARY OF THE APPLICATION

Some embodiments of the present invention provide a system and methods for treating Alzheimer's disease by enhancing the clearance of waste products from the brain. The system comprises central electrodes, peripheral electrodes, and control circuitry, which is electrically coupled to the electrodes. For some applications, a method for treating Alzheimer's disease comprises:

disposing the central electrodes outside and in electrical contact with a skull of a head of a subject identified as at risk of or suffering from Alzheimer's disease, within one cm of a sagittal midplane of the skull;

disposing the peripheral electrodes outside and in electrical contact with the skull, superior to an orbitomeatal plane of the skull and inferior to a first plane midway between the orbitomeatal plane and a cranial vertex of the skull, the first plane parallel to the orbitomeatal plane; and treating the subject by clearing a substance from brain parenchyma to a subarachnoid space, the substance selected from the group consisting of: amyloid beta, tau protein, and metal ions, by activating control circuitry to (i) apply respective currents between one or more of the central electrodes and two or more of the peripheral electrodes, and (ii) configure the central electrodes as cathodes and the peripheral electrodes as anodes.

Typically, after being cleared to the subarachnoid space by the applied currents, the substance is naturally drained with cerebrospinal fluid (CSF) from the subarachnoid space to a superior sagittal sinus (through arachnoid granulations and villi).

For some applications, the peripheral electrodes comprise left peripheral electrodes and right peripheral electrodes, adapted to be disposed outside and in electrical contact with the skull, left and right of the sagittal midplane, respectively, superior to the orbitomeatal plane and inferior to the first plane. The control circuitry is configured to treat the subject by (i) applying the respective currents (a) between the one or more of the central electrodes and one or more of the left peripheral electrodes and (b) between one or more of the central electrodes and one or more of the right peripheral electrodes, and (ii) configuring the central electrodes as the cathodes, the left peripheral electrodes as anodes, and the right peripheral electrodes as anodes. For some of these applications, the control circuitry is activated to independently apply the respective currents to (a) respective pairs of the central electrodes and the left peripheral electrodes and (b) respective pairs of the central electrodes and the right peripheral electrodes.

In experiments conducted on behalf of the inventor, amyloid beta was found to be attracted to the positive electrode (anode).

There is therefore provided, in accordance with an Inventive Concept 1 of the present invention, a method including:

disposing central electrodes outside and in electrical contact with a skull of a head of a subject identified as at risk of or suffering from Alzheimer's disease, within one cm of a sagittal midplane of the skull;

disposing peripheral electrodes outside and in electrical contact with the skull, superior to an orbitomeatal plane of the skull and inferior to a first plane midway between the orbitomeatal plane and a cranial vertex of the skull, the first plane parallel to the orbitomeatal plane; and treating the subject by clearing a substance from brain parenchyma to a subarachnoid space, the substance selected from the group consisting of: amyloid beta, tau protein, and metal ions, by activating control circuitry to:

apply respective currents between one or more of the central electrodes and two or more of the peripheral electrodes, and configure the central electrodes as cathodes and the peripheral electrodes as anodes.

Inventive Concept 2. The method according to Inventive Concept 1, wherein the substance is the amyloid beta, and wherein clearing the substance includes clearing the amyloid beta from the brain parenchyma to the subarachnoid space.

Inventive Concept 3. The method according to Inventive Concept 1, wherein the substance is the tau protein, and wherein clearing the substance includes clearing the tau protein from the brain parenchyma to the subarachnoid space.

Inventive Concept 4. The method according to Inventive Concept 1, wherein disposing the peripheral electrodes includes disposing the peripheral electrodes inferior to a second plane located at a distance from the orbitomeatal plane equal to 40% of a distance between the orbitomeatal plane and the cranial vertex, the second plane parallel to the orbitomeatal plane.

Inventive Concept 5. The method according to Inventive Concept 1, wherein disposing the peripheral electrodes includes disposing the peripheral electrodes superior to a third plane located at a distance from the orbitomeatal plane equal to 5% of a distance between the orbitomeatal plane and the cranial vertex, the third plane parallel to the orbitomeatal plane.

Inventive Concept 6. The method according to Inventive Concept 5, wherein the third plane is located at a distance from the orbitomeatal plane equal to 10% of the distance between the orbitomeatal plane and the cranial vertex.

Inventive Concept 7. The method according to Inventive Concept 1, wherein disposing the central electrodes and the peripheral electrodes includes disposing all of the central electrodes superior to all of the peripheral electrodes.

Inventive Concept 8. The method according to Inventive Concept 1, wherein disposing the central electrodes and the peripheral electrodes includes disposing at least 90% of the central electrodes superior to all of the peripheral electrodes.

Inventive Concept 9. The method according to Inventive Concept 1, wherein disposing the central electrodes and the peripheral electrodes includes disposing the central electrodes at respective distances from respective closest ones of the peripheral electrodes, the distances measured along an external surface of the head, each of the distances at least 4 cm.

Inventive Concept 10. The method according to Inventive Concept 1, wherein disposing the central electrodes and the peripheral electrodes includes disposing the central electrodes at respective distances from respective closest ones of the peripheral electrodes, the distances measured along an external surface of the head, at least 90% of the distances at least 4 cm.

Inventive Concept 11. The method according to Inventive Concept 1, wherein disposing the peripheral electrodes includes disposing an anterior-most one of the peripheral electrodes within a distance from the sagittal midplane, the distance measured along an external surface of the head, the distance no more than 5 cm.

Inventive Concept 12. The method according to Inventive Concept 1, wherein disposing the peripheral electrodes includes disposing a posterior-most one of the peripheral electrodes within a distance from the sagittal midplane, the distance measured along an external surface of the head, the distance no more than 5 cm.

Inventive Concept 13. The method according to Inventive Concept 1,
  wherein the peripheral electrodes include left peripheral electrodes and right peripheral electrodes,
  wherein disposing the peripheral electrodes includes disposing the left peripheral electrodes and right peripheral electrodes outside and in electrical contact with the skull, left and right of the sagittal midplane, respectively, superior to the orbitomeatal plane and inferior to the first plane, and
  wherein activating the control circuitry includes activating the control circuitry to:
    apply the respective currents (a) between the one or more of the central electrodes and one or more of the left peripheral electrodes and (b) between one or more of the central electrodes and one or more of the right peripheral electrodes, and
    configure the central electrodes as the cathodes, the left peripheral electrodes as anodes, and the right peripheral electrodes as anodes.

Inventive Concept 14. The method according to Inventive Concept 13, wherein disposing the left peripheral electrodes and the right peripheral electrodes includes disposing a left anterior-most one of the left peripheral electrodes and a right anterior-most one of the right peripheral electrodes, respectively, within respective distances from the sagittal midplane, the distances measured along an external surface of the head, each of the distances no more than 5 cm.

Inventive Concept 15. The method according to Inventive Concept 13, wherein disposing the left peripheral electrodes and the right peripheral electrodes includes disposing a left posterior-most one of the left peripheral electrodes and a right posterior-most one of the right peripheral electrodes, respectively, within respective distances from the sagittal midplane, the distances measured along an external surface of the head, each of the distances no more than 5 cm.

Inventive Concept 16. The method according to Inventive Concept 13, wherein disposing the left peripheral electrodes and the right peripheral electrodes includes disposing at least five left peripheral electrodes and at least five right peripheral electrodes, respectively.

Inventive Concept 17. The method according to Inventive Concept 13, wherein activating the control circuitry to apply the respective currents (a) between the one or more of the central electrodes and the one or more of the left peripheral electrodes and (b) between the one or more of the central electrodes and the one or more of the right peripheral electrodes includes activating the control circuitry to apply:
  a first current between a first one of the central electrodes and a first one of the left peripheral electrodes,
  a second current between the first one of the central electrodes and a first one of the right peripheral electrodes,
  a third current between a second one of the central electrodes and a second one of the left peripheral electrodes, and
  a fourth current between the second one of the central electrodes and a second one of the right peripheral electrodes.

Inventive Concept 18. The method according to Inventive Concept 1,
  wherein the peripheral electrodes are left peripheral electrodes,
  wherein disposing the peripheral electrodes includes disposing the left peripheral electrodes outside and in electrical contact with the skull, left of the sagittal midplane, superior to the orbitomeatal plane and inferior to the first plane, and
  wherein activating the control circuitry includes activating the control circuitry to:
    apply the respective currents between the one or more of the central electrodes and two or more of the left peripheral electrodes, and
    configure the central electrodes as the cathodes and the left peripheral electrodes as the anodes.

Inventive Concept 19. The method according to Inventive Concept 18, wherein all of the peripheral electrodes are the left peripheral electrodes, and wherein the method does not include disposing any of the peripheral electrodes more than one cm right of the sagittal midplane of the skull.

Inventive Concept 20. The method according to Inventive Concept 18, wherein disposing the left peripheral electrodes includes disposing the left peripheral electrodes in a first series and a second series, the left peripheral electrodes of the first series located at least a distance superior to the left peripheral electrodes of the second series, the distance measured along an external surface of the head, and the distance at least 3 cm.

Inventive Concept 21. The method according to Inventive Concept 1, wherein activating the control circuitry to apply the respective currents includes activating the control circuitry to set the respective currents to have respective amplitudes of 1-5 milliamps.

Inventive Concept 22. The method according to Inventive Concept 1, wherein activating the control circuitry to apply the respective currents includes activating the control circuitry to set each of the respective currents to the lesser of (a) a predefined maximum current and (b) a current that results from application of a predefined maximum voltage.

Inventive Concept 23. The method according to Inventive Concept 22, wherein the predefined maximum voltage is 2-15 V.

Inventive Concept 24. The method according to Inventive Concept 1, wherein disposing the peripheral electrodes includes disposing peripheral electrodes outside the head.

Inventive Concept 25. The method according to Inventive Concept 24, wherein disposing the peripheral electrodes includes disposing the peripheral electrodes on an external surface of the head.

Inventive Concept 26. The method according to Inventive Concept 1, wherein disposing the peripheral electrodes includes implanting the peripheral electrodes under skin of the head.

Inventive Concept 27. The method according to Inventive Concept 1, wherein disposing the central electrodes includes disposing the central electrodes outside the head.

Inventive Concept 28. The method according to Inventive Concept 27, wherein disposing the central electrodes includes disposing the central electrodes on an external surface of the head.

Inventive Concept 29. The method according to Inventive Concept 1, wherein disposing the central electrodes includes implanting the central electrodes under skin of the head.

Inventive Concept 30. The method according to Inventive Concept 1, wherein disposing the central electrodes includes disposing at least five central electrodes.

Inventive Concept 31. The method according to Inventive Concept 1, wherein disposing the peripheral electrodes includes disposing at least five peripheral electrodes.

Inventive Concept 32. The method according to Inventive Concept 1, wherein activating the control circuitry includes activating the control circuitry to apply the respective currents to as respective DC currents.

There is further provided, in accordance with an Inventive Concept 33 of the present invention, an electrical substance-clearance system for treating a subject identified as at risk of or suffering from Alzheimer's disease, the system including:

central electrodes, adapted to be disposed outside and in electrical contact with a skull of a head of the subject, within one cm of a sagittal midplane of the skull;

peripheral electrodes, adapted to be disposed outside and in electrical contact with the skull, superior to an orbitomeatal plane of the skull and inferior to a first plane midway between the orbitomeatal plane and a cranial vertex of the skull, the first plane parallel to the orbitomeatal plane; and control circuitry, configured to treat the subject by clearing a substance from brain parenchyma to a subarachnoid space, the substance selected from the group consisting of: amyloid beta, tau protein, and metal ions, by:

applying respective currents between one or more of the central electrodes and two or more of the peripheral electrodes, and configuring the central electrodes as cathodes and the peripheral electrodes as anodes.

Inventive Concept 34. The system according to Inventive Concept 33, wherein the substance is the amyloid beta, and wherein the control circuitry is configured to clearing the amyloid beta from the brain parenchyma to the subarachnoid space.

Inventive Concept 35. The system according to Inventive Concept 33, wherein the substance is the tau protein, and wherein the control circuitry is configured to clearing the tau protein from the brain parenchyma to the subarachnoid space.

Inventive Concept 36. The system according to Inventive Concept 33, wherein the system further includes (a) a central lead, which is adapted to be disposed outside the skull, and (b) a peripheral lead, adapted to be disposed outside the skull, superior to the orbitomeatal plane and inferior to the first plane, wherein the system includes at least five central electrodes that are disposed along the central lead, and wherein the system includes at least five peripheral electrodes that are disposed along the peripheral lead.

Inventive Concept 37. The system according to Inventive Concept 33, wherein the control circuitry is configured to apply the respective currents as respective DC currents.

Inventive Concept 38. The system according to Inventive Concept 33, wherein the control circuitry is configured to limit, to maximum value, an amplitude of each of the respective currents, the maximum value 1-5 milliamps.

Inventive Concept 39. The system according to Inventive Concept 33, wherein the control circuitry is configured to apply the respective currents by applying respective voltages, each of which equals the lesser of (a) a predefined maximum voltage and (b) a voltage that results in a current having a predefined maximum amplitude.

Inventive Concept 40. The system according to Inventive Concept 39, wherein the predefined maximum voltage is 2-15 V.

Inventive Concept 41. The system according to any one of Inventive Concepts 33-40, wherein the peripheral electrodes include left peripheral electrodes and right peripheral electrodes, adapted to be disposed outside and in electrical contact with the skull, left and right of the sagittal midplane, respectively, superior to the orbitomeatal plane and inferior to the first plane, and wherein the control circuitry is configured to treat the subject by:

applying the respective currents (a) between the one or more of the central electrodes and one or more of the left peripheral electrodes and (b) between one or more of the central electrodes and one or more of the right peripheral electrodes, and configuring the central electrodes as the cathodes, the left peripheral electrodes as anodes, and the right peripheral electrodes as anodes.

Inventive Concept 42. The system according to Inventive Concept 41, wherein the left peripheral electrodes include at least five left peripheral electrodes, and wherein the right peripheral electrodes include at least five right peripheral electrodes.

Inventive Concept 43. The system according to Inventive Concept 41,
wherein the system further includes (a) a central lead, which is adapted to be disposed outside the skull, and (b) a left peripheral lead and a right peripheral lead, adapted to be disposed outside the skull, left and right of the sagittal midplane, respectively, superior to the orbitomeatal plane and inferior to the first plane,
wherein the system includes at least five central electrodes that are disposed along the central lead, and
wherein the system includes at least five left peripheral electrodes and at least five right peripheral electrodes that are disposed along the left peripheral lead and the right peripheral lead, respectively.

Inventive Concept 44. The system according to Inventive Concept 41, wherein the control circuitry is configured to apply the one or more currents between (a) the one or more of the central electrodes and (b) the one or more of the peripheral electrodes includes activating the control circuitry to apply:
a first current between a first one of the central electrodes and a first one of the left peripheral electrodes,
a second current between the first one of the central electrodes and a first one of the right peripheral electrodes,
a third current between a second one of the central electrodes and a second one of the left peripheral electrodes, and
a fourth current between the second one of the central electrodes and a second one of the right peripheral electrodes.

Inventive Concept 45. The system according to any one of Inventive Concepts 33-40,
wherein the peripheral electrodes are left peripheral electrodes, which are adapted to be disposed outside and in electrical contact with the skull, left of the sagittal midplane, superior to the orbitomeatal plane and inferior to the first plane, and
wherein the control circuitry is configured to treat the subject by:
applying the respective currents between the one or more of the central electrodes and two or more of the left peripheral electrodes, and
configuring the central electrodes as the cathodes and the left peripheral electrodes as the anodes.

Inventive Concept 46. The system according to Inventive Concept 45, wherein all of the peripheral electrodes are the left peripheral electrodes, and wherein the system does not include any right peripheral electrodes adapted to be disposed more than one cm right of the sagittal midplane of the skull.

Inventive Concept 47. The system according to Inventive Concept 45, wherein the left peripheral electrodes include a first series of the left peripheral electrodes and a second series of the left peripheral electrodes, adapted to be disposed outside and in electrical contact with the skull such that the left peripheral electrodes of the first series are located at least a distance superior to the left peripheral electrodes of the second series, the distance measured along an external surface of the head, and the distance at least 3 cm.

Inventive Concept 48. The system according to any one of Inventive Concepts 33-40, wherein the peripheral electrodes are adapted to be disposed outside the head.

Inventive Concept 49. The system according to Inventive Concept 48, wherein the peripheral electrodes are adapted to be disposed on an external surface of the head.

Inventive Concept 50. The system according to any one of Inventive Concepts 33-40, wherein the peripheral electrodes are adapted to be implanted under skin of the head.

Inventive Concept 51. The system according to any one of Inventive Concepts 33-40, wherein the central electrodes are adapted to be disposed outside the head.

Inventive Concept 52. The system according to Inventive Concept 51, wherein the central electrodes are adapted to be disposed on an external surface of the head.

Inventive Concept 53. The system according to any one of Inventive Concepts 33-40, wherein the central electrodes are adapted to be implanted under skin of the head.

The present invention will be more fully understood from the following detailed description of embodiments thereof, taken together with the drawings, in which:

DETAILED DESCRIPTION OF APPLICATIONS

Figure 1A:
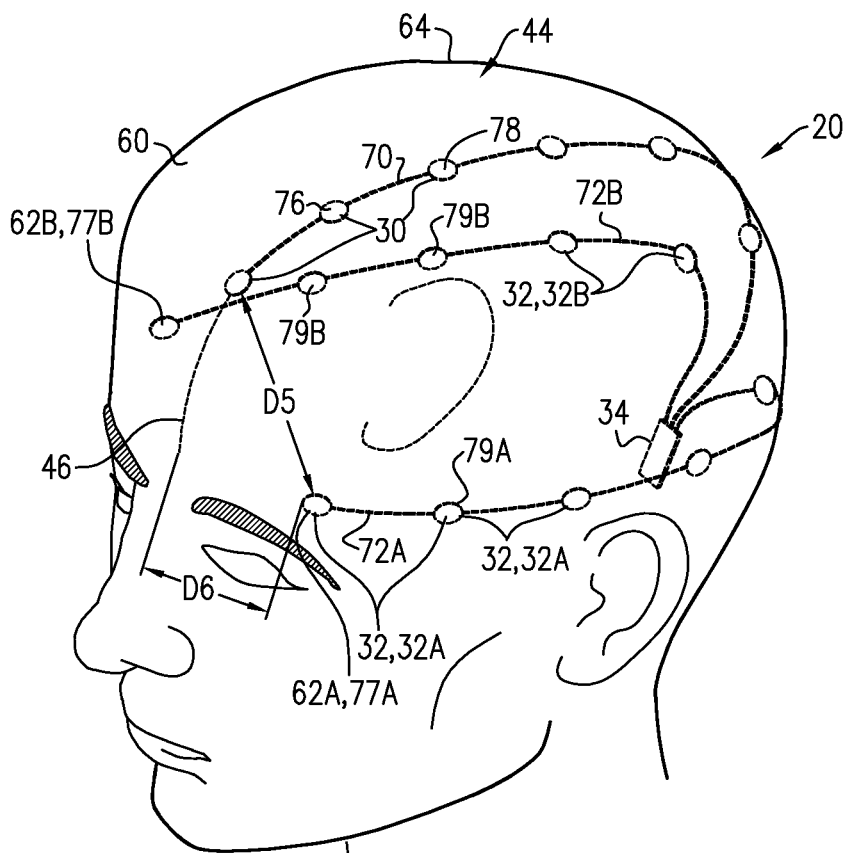
FIGS. 1A-B are schematic illustration of a system for treating Alzheimer's disease applied to a head of a subject, in accordance with respective applications of the present invention.
Figure 1B:
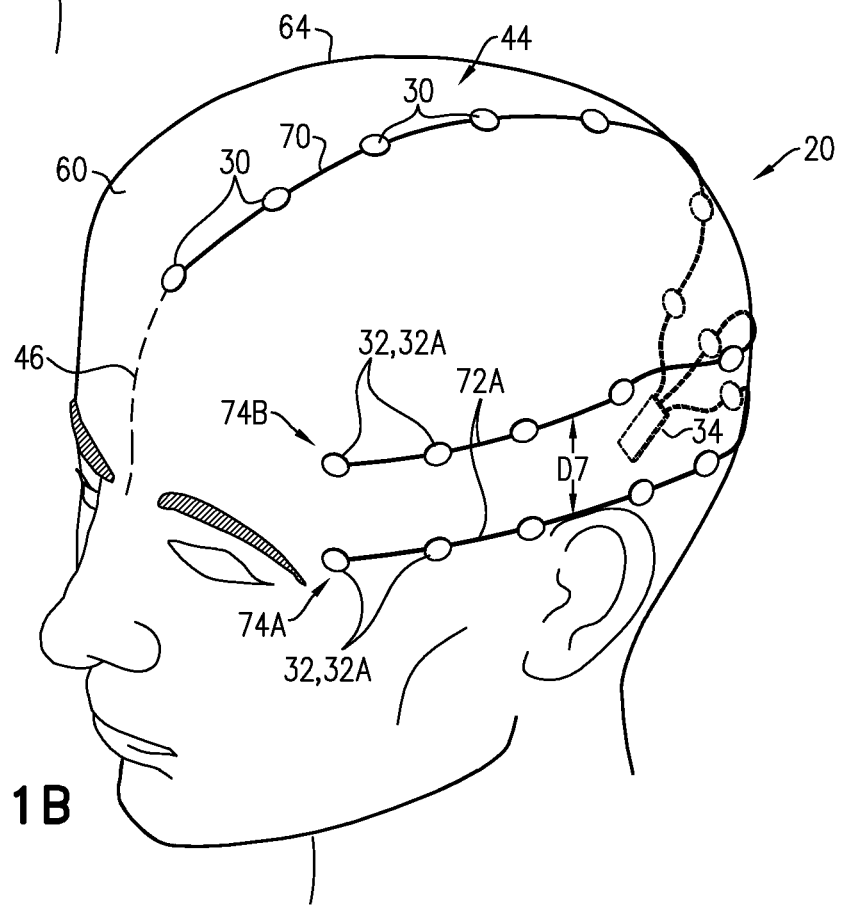

FIGS. 1A-B are schematic illustration of a system 20 for treating Alzheimer's disease applied to a head 44 of a subject, in accordance with respective applications of the present invention. System 20 comprises central electrodes 30, such as at least 5, no more than 20, and/or 5-20 central electrodes 30; and peripheral electrodes 32.

For some applications, peripheral electrodes 32 comprise:
left peripheral electrodes 32A, such as at least 5, no more than 40, and/or 5-40 left peripheral electrodes 32A, such as 5-20 left peripheral electrodes 32A, or 10-40 left peripheral electrodes 32A; and
right peripheral electrodes 32B, such as at least 5, no more than 40, and/or 5-40 right peripheral electrodes 32B, such as 5-20 right peripheral electrodes 32B, or 10-40 right peripheral electrodes 32B.

For clarity of illustration, right peripheral electrodes 32B are not shown in FIG. 1B.

For some applications, the number of each type of electrode is determined based on the size of head 44 of the subject. System 20 further comprises control circuitry 34, which is electrically coupled to the electrodes.

Figure 2:
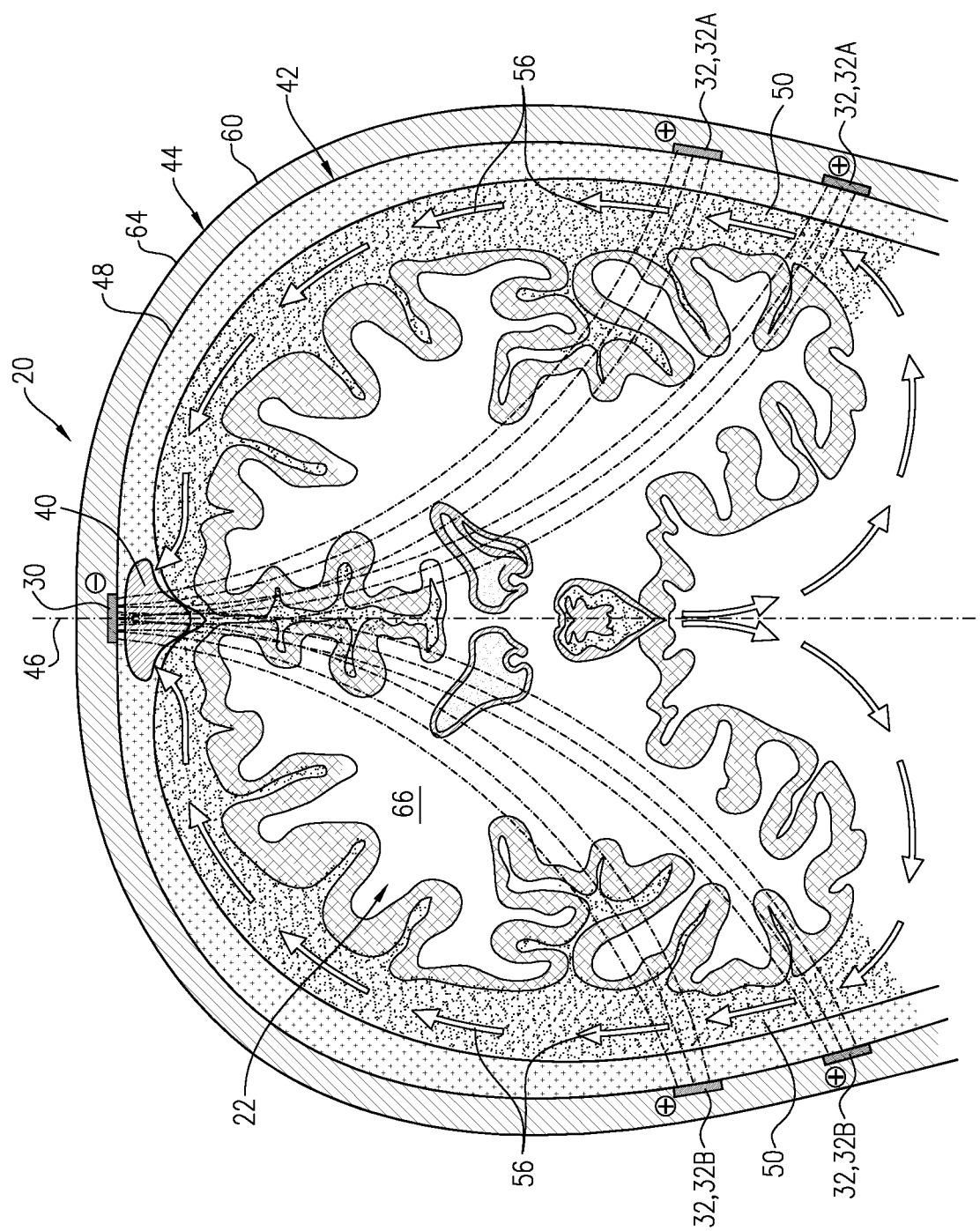
FIG. 2 is a schematic cross-sectional illustration of central electrodes and left and right peripheral electrodes of the system of FIGS. 1A-B applied to a head, including a brain, in accordance with an application of the present invention.

Reference is still made to FIGS. 1A-B, and is further made to FIG. 2, which is a schematic cross-sectional illustration of central electrodes 30 and peripheral electrodes 32 (e.g., left and right peripheral electrodes 32A and 32B) applied to head 44, including a brain 22, in accordance with an application of the present invention.

Figure 3:
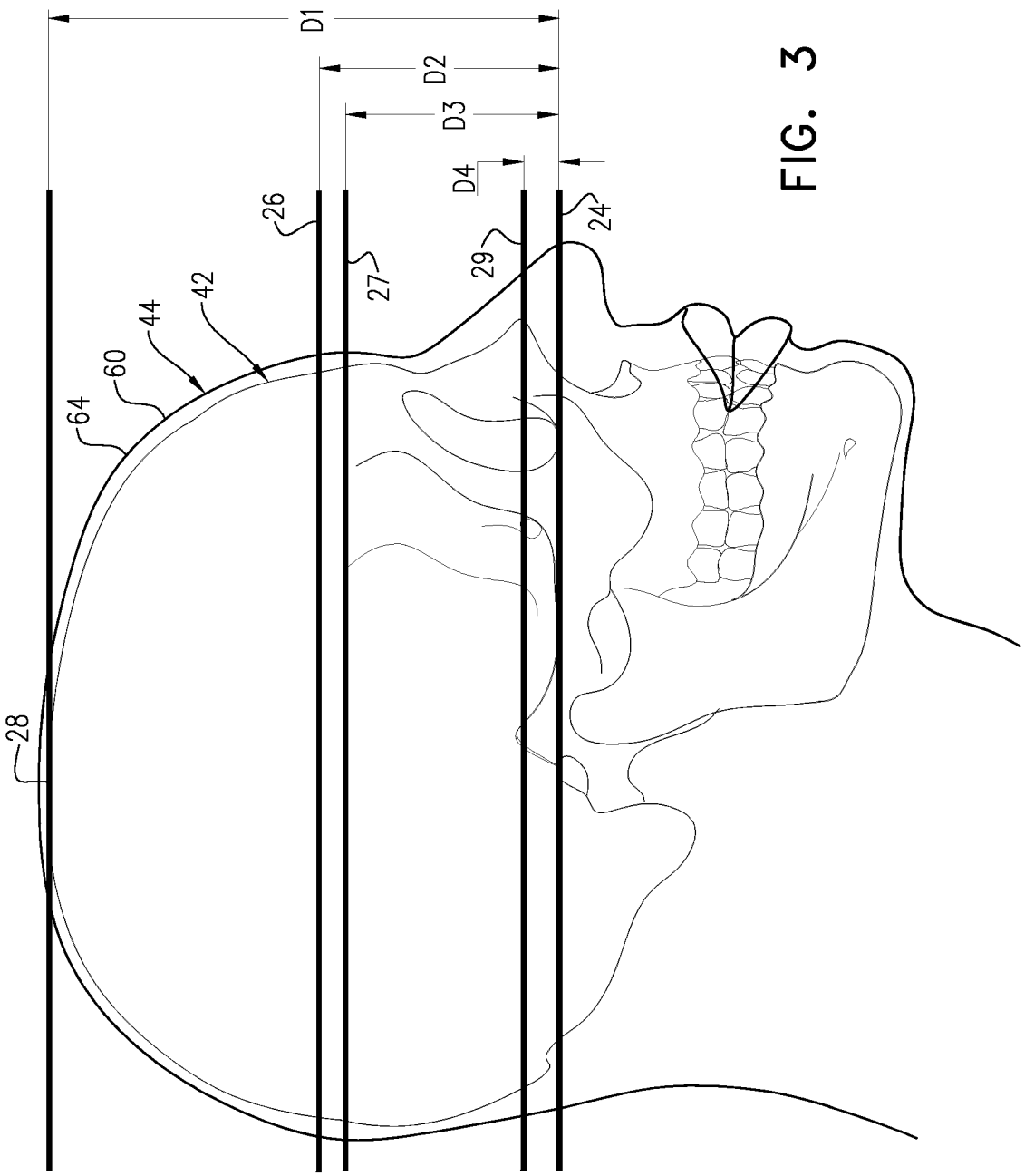
FIG. 3 is a schematic cross-sectional illustration of the head of FIGS. 1A-B and 2, including a skull, in accordance with an application of the present invention.

Reference is still further made to FIG. 3, which is a schematic cross-sectional illustration of head 44, including a skull 42, in accordance with an application of the present invention.

For some applications, a method for treating Alzheimer's disease comprises:
  disposing central electrodes 30 outside and in electrical contact with skull 42 of head 44 of a subject identified as at risk of or suffering from Alzheimer's disease, within one cm of a sagittal midplane 46 (labeled in FIGS. 1A-B and 2) of skull 42 (e.g., directly over sagittal midplane 46, such as shown); the one cm is measured along an external surface 48 of skull 42;
  disposing peripheral electrodes 32 outside and in electrical contact with skull 42, superior to an orbitomeatal plane 24 (also known as a Frankfort plane) of skull 42 and inferior to a first plane 26 midway between orbitomeatal plane 24 and a cranial vertex 28 of skull 42, first plane 26 parallel to orbitomeatal plane 24 (labeled in FIG. 3); and
  treating the subject by clearing a substance from brain parenchyma 66 to a subarachnoid space 50 (labeled in FIG. 2), as schematically illustrated in FIG. 3, by activating control circuitry 34 to (i) apply respective currents between one or more of central electrodes 30 and two or more of peripheral electrodes 32, and (ii) configure central electrodes 30 as cathodes and peripheral electrodes 32 as anodes.

Typically, the substance is amyloid beta, tau protein, and/or metal ions.

Typically, after being cleared to subarachnoid space 50 by the applied currents, the substance is naturally drained with cerebrospinal fluid (CSF) from subarachnoid space 50 to a superior sagittal sinus 40 (through arachnoid granulations and villi). (It is noted that the natural flow of CSF within subarachnoid space 50 toward superior sagittal sinus 40, schematically illustrated in FIG. 2 by arrows 56, overcomes any minimal driving of the substance in the opposite direction that may be caused by the applied currents.)

Typically, central electrodes 30 are disposed over or near a superior sagittal sinus 40. As used in the present application, including in the claims and Inventive Concepts, "over the superior sagittal sinus" means aligned with the superior sagittal sinus at a location more superficial than the superior sagittal sinus, i.e., at a greater distance from a center of the head.

As used in the present application, including the claims and Inventive Concepts, "treating" includes both treating a subject already diagnosed with a disease, as well as preventing the development of the disease in a subject not diagnosed with the disease and/or asymptomatic for the disease (for example, the disease may be Alzheimer's disease, cerebral amyloid angiopathy (CAA), or hydrocephalus, such as normal pressure hydrocephalus). In the case of normal pressure hydrocephalus, the electrical treatment described herein may help increase flow of cerebrospinal fluid (CSF) through clogged arachnoid granulations, such as because of the negative charge of central electrodes 30.

For some applications:
  disposing peripheral electrodes 32 comprises disposing left peripheral electrodes 32A and right peripheral electrodes 32B outside and in electrical contact with skull 42, left and right of sagittal midplane 46, respectively, superior to orbitomeatal plane 24 and inferior to first plane 26, and
  control circuitry 34 is activated to (i) apply respective currents (a) between one or more of central electrodes 30 and one or more of left peripheral electrodes 32A and (b) between one or more of central electrodes 30 and one or more of right peripheral electrodes 32B, and (ii) configure central electrodes 30 as the cathodes, left peripheral electrodes 32A as anodes, and right peripheral electrodes 32B as anodes.

Reference is made to FIG. 3. As mentioned above, first plane 26 is midway between orbitomeatal plane 24 and cranial vertex 28. In other words, first plane 26 is located at a distance D2 from orbitomeatal plane 24 equal to 50% of a distance D1 between orbitomeatal plane 24 and cranial vertex 28.

Reference is still made to FIG. 3. For some applications, peripheral electrodes 32 (e.g., left peripheral electrodes 32A and right peripheral electrodes 32B) are disposed inferior to a second plane 27 located at a distance D3 from orbitomeatal plane 24 equal to 45%, e.g., 40%, such as 35%, of the distance D1 between orbitomeatal plane 24 and cranial vertex 28. Second plane 27 is parallel to orbitomeatal plane 24.

For some applications, peripheral electrodes 32 (e.g., left peripheral electrodes 32A and right peripheral electrodes 32B) are disposed superior to a third plane 29 located at a distance D4 from orbitomeatal plane 24 equal to 5%, e.g., 10%, of the distance D1 between orbitomeatal plane 24 and cranial vertex 28. Third plane 29 is parallel to orbitomeatal plane 24.

Reference is again made to FIGS. 1A-B and 2. For some applications, peripheral electrodes 32 are left peripheral electrodes 32A, which are adapted to be disposed outside and in electrical contact with skull 42, left of sagittal midplane 46, superior to orbitomeatal plane 24 and inferior to first plane 26. Control circuitry 34 is configured to treat the subject by applying the respective currents between the one or more of central electrodes 30 and two or more of left peripheral electrodes 32A, and configuring central electrodes 30 as the cathodes and left peripheral electrodes 32A as the anodes. For some of these applications, all of peripheral electrodes 32 are left peripheral electrodes 32A, and system 20 does not comprise any right peripheral electrodes 32B adapted to be disposed more than one cm right of sagittal midplane 46 of skull 42. Similarly, for some applications, peripheral electrodes 32 are right peripheral electrodes 32B, and system 20 has the other features described in this paragraph mutatis mutandis.

Providing peripheral electrodes 32 on a single side of skull 42 may be appropriate, for example, for personalizing therapy for a patient whose brain has amyloid plaques on only one side, or primarily only on one side. For example, the location of the amyloid plaques may be ascertained using amyloid positive emission tomography (PET), as is known in the art.

Reference is still made to FIGS. 1A-B and 2. For some applications, all of central electrodes 30 are disposed superior to all of peripheral electrodes 32 (e.g., all of left peripheral electrodes 32A and all of right peripheral electrodes 32B). Alternatively, for some applications, at least 90% of central electrodes 30 are disposed superior to all of peripheral electrodes 32 (e.g., all of left peripheral electrodes 32A and all of right peripheral electrodes 32B). Further alternatively, fewer than 90% of central electrodes 30 are disposed superior to all of peripheral electrodes 32 (e.g., all of left peripheral electrodes 32A and all of right peripheral electrodes 32B).

Reference is made to FIG. 1A. For some applications, central electrodes 30 are disposed at respective distances D5 from respective closest one of peripheral electrodes 32 (e.g., respective closest ones 62A and 62B of left peripheral electrodes 32A and right peripheral electrodes 32B), the distances D5 measured along an external surface 60 of head 44, each of the distances D5 at least 4 cm, such as at least 5 cm, e.g., at least 6 cm. Alternatively, for some applications, at least 90% of the distances D5 are at least 4 cm, such as at least 5 cm, e.g., at least 6 cm. Further alternatively, fewer than least 90% of the distances D5 are at least 4 cm, such as at least 5 cm, e.g., at least 6 cm.

Reference is still made to FIG. 1A. For some applications, an anterior-most one of peripheral electrodes 32 is disposed within a distance D6 from sagittal midplane 46, the distance D6 measured along external surface 60 of head 44, and the distance D6 no more than 5 cm, such as no more than 4 cm, e.g., no more than 3 cm. For some applications, a left anterior-most one 68A of left peripheral electrodes 32A and a right anterior-most one 68B of right peripheral electrodes 32B, respectively, are disposed within respective distances D6 from sagittal midplane 46, the distances D6 measured along external surface 60 of head 44, each of the distances D6 no more than 5 cm, such as no more than 4 cm, e.g., no more than 3 cm. (For clarity of illustration, D6 is labeled in FIG. 1A for only the left side.)

Reference is still made to FIG. 1A. For some applications, a posterior-most one of peripheral electrodes 32 is disposed within a distance from sagittal midplane 46, the distance measured along external surface 60 of head 44, and the distance no more than 5 cm, such as no more than 4 cm, e.g., no more than 3 cm. For some applications, a left posterior-most one of left peripheral electrodes 32A and a right posterior-most one of right peripheral electrodes 32B, respectively, are disposed within respective distances from sagittal midplane 46, the distances measured along external surface 60 of head 44, each of the distances no more than 5 cm, such as no more than 4 cm, e.g., no more than 3 cm.

Reference is still made to FIG. 1A. For some applications, left peripheral electrodes 32A are disposed such that at least one of left peripheral electrodes 32A is at least 1 cm, no more than 5 cm, and/or 1-5 cm (e.g., 3 cm) from another one of left peripheral electrodes 32A, and/or right peripheral electrodes 32B are disposed such that at least one of right peripheral electrodes 32B is at least 1 cm, no more than 5 cm, and/or 1-5 cm (e.g., 3 cm) from another one of right peripheral electrodes 32B. Alternatively or additionally, for some applications, left peripheral electrodes 32A are disposed such that longitudinally-adjacent ones of the electrodes are disposed at least 1 cm, no more than 5 cm, and/or 1-5 cm (e.g., 3 cm) from each other, and/or right peripheral electrodes 32B are disposed such that longitudinally-adjacent ones of the electrodes are disposed at least 1 cm, no more than 5 cm, and/or 1-5 cm (e.g., 3 cm) from each other.

For some applications, system 20 further comprises (a) a central lead 70, which is adapted to be disposed outside skull 42, and (b) a peripheral lead, adapted to be disposed outside skull 42, superior to orbitomeatal plane 24 and inferior to first plane 26. Central electrodes 30 are disposed (e.g., fixed) along central lead 70, and peripheral electrode 32 are disposed (e.g., fixed) along the peripheral leads. For some applications, system 20 comprises a left peripheral lead 72A and a right peripheral lead 72B, adapted to be disposed outside skull 42, left and right of sagittal midplane 46, respectively, superior to orbitomeatal plane 24 and inferior to first plane 26. Left and right peripheral electrodes 32A and 32B are disposed (e.g., fixed) along left and right peripheral leads 72A and 72B, respectively.

For some applications, system 20 comprises at least five central electrodes 30 that are disposed along central lead 70, and at least five peripheral electrodes 32A that are disposed along the peripheral lead. For some applications, system 20 comprises at least five central electrodes 30 that are disposed along central lead 70, and at least five left peripheral electrodes 32A and at least five right peripheral electrodes 32B that are disposed along left peripheral lead 72A and right peripheral lead 72B, respectively. As a result, the electrical field generated by the applied currents typically passes through large portions of the brain.

Reference is again made to FIGS. 1A-B. For some applications, such as shown in FIG. 1A, central electrodes 30 and/or peripheral electrodes 32 (e.g., left peripheral electrodes 32A and/or right peripheral electrodes 32B) are implanted under skin 64 of head 44. For other applications, such as shown in FIG. 1B, central electrodes 30 and/or peripheral electrodes 32 (e.g., left peripheral electrodes 32A and/or right peripheral electrodes 32B) are disposed outside head 44, such as on an external surface 60 of head 44.

For some applications in which central electrodes 30 are implanted under skin 64 and disposed along central lead 70, the implantation is performed by introducing central lead 70 through an incision in skin 64, typically at a posterior site of the head, and tunneling the central lead toward an anterior site of the head, such as near the forehead. Optionally, each of central electrodes 30 is inserted through a respective incision in skin 64, and connected to central lead 70.

For some applications in which left peripheral electrodes 32A and/or right peripheral electrodes 32B are implanted under skin 64 and disposed along left and right peripheral leads 72A and 72B, respectively, the implantation is performed by introducing left and right peripheral leads 72A and 72B through respective incisions in skin 64, typically at a posterior site of the head, and tunneling the leads toward an anterior site of the head, such as near the forehead. Optionally, each of left peripheral electrodes 32A and/or right peripheral electrodes 32B is inserted through a respective incision in skin 64, and connected to their respective lead.

For some applications, the method further comprises implanting control circuitry 34 under skin of the subject, such as under skin 64 of head 44, or elsewhere in the subject's body.

Reference is made to FIG. 1B. For some applications, left peripheral electrodes 32A are disposed in a first series 74A and a second series 74B, left peripheral electrodes 32A of first series 74A located at least a distance D7 superior to left peripheral electrodes 32A of second series 74B, the distance D7 measured along external surface 60 of head 44, and the distance D7 at least 3 cm, such as at least 4 cm, and optionally no more than 5 cm. Typically, respective separate left peripheral leads 72A are provided for the two series. Alternatively or additionally, right peripheral electrodes 32B may be disposed in this two-series manner.

Although the following configuration is described with reference to FIG. 1A, it is equally applicable to the configuration of FIG. 1B, mutatis mutandis. For some applications, control circuitry 34 is activated to independently apply the respective currents between (a) respective pairs of central electrodes 30 and left peripheral electrodes 32A and (b) respective pairs of central electrodes 30 and right peripheral electrodes 32B. Optionally, one or more of the pairs includes the same respective central electrode 30 paired with both a left peripheral electrode 32A and a right peripheral electrode 32B; in other words, control circuitry 34 may be activated to apply the respective currents, either at the same time or at different times, between each of central electrodes 30 and both (a) a corresponding one of left peripheral electrodes 32A and (b) a corresponding one of right peripheral electrodes 32B.

For example, control circuitry 34 may be activated to apply:
- a first current between a first one 76 of central electrodes 30 and a first one 77A of left peripheral electrodes 32A,
- a second current between the first one 76 of central electrodes 30 and a first one 77B of right peripheral electrodes 32B,
- a third current between a second one 78 of central electrodes 30 and a second one 79A of left peripheral electrodes 32A, and
- a fourth current between the second one 78 of central electrodes 30 and a second one 79B of right peripheral electrodes 32B.

Such independent application of the currents may allow continued effective operation of system 20 even if a low resistance should develop between the electrodes of one of the pairs (e.g., because of anatomical variations).

For some applications, control circuitry 34 is activated to drive the respective currents through pairs of central electrodes 30 and right peripheral electrodes 32 such that stronger currents are driven through areas of the brain with amyloid plaques (e.g., ascertained with amyloid PET), and that weaker currents are applies elsewhere, such as for preventive treatment.

For some of these applications, in order to enable such independent application of the currents, central lead 70 comprises a plurality of conductive wires corresponding to a number of central electrodes 30, left peripheral lead 72A comprises a plurality of conductive wires corresponding to a number of left peripheral electrodes 32A, and/or right peripheral lead 72B comprises a plurality of conductive wires corresponding to a number of right peripheral electrodes 32B. Alternatively, control circuitry 34 and the electrodes implement electrical multiplexing, as is known in the art, in which case each of the leads need only comprise a single conductive wire. Alternatively, for some applications, all of central electrodes 30 are electrically coupled to one another (such as by a single conductive wire in the central lead), all of left peripheral electrodes 32A, and/or all of right peripheral electrodes 32B are electrically coupled to one other (such as by respective single conductive wires in the peripheral leads).

For some applications, control circuitry 34 is configured to set each of the respective currents to have respective amplitudes of at least 1 milliamp, no more than 5 milliamps (e.g., no more than 3 milliamps), and/or 1-5 milliamps, such as 1-3 milliamps; or at least 0.5 milliamps, such as 0.5-5 milliamps, e.g., 0.5-3 milliamps.

For some applications, control circuitry 34 is configured to set each of the respective currents to the lesser of (a) a predefined maximum current and (b) a current that results from application of a predefined maximum voltage. For some applications, the predefined maximum voltage is 2-15 V. This maximum voltage typically results in a voltage within the brain tissue of no more than 1.2 V, such as because of (a) the impedance of the interface between the electrodes and the tissue, and/or (b) the impedance of the peripheral tissues of the head, such as the skull and the skin.

For some applications, control circuitry 34 is configured to apply the respective currents as respective DC currents.

For some applications, control circuitry 34 is activated to apply the respective currents in treatment sessions, each of which has a duration of several seconds or several minutes, or continuously for longer periods (e.g., 30 minutes). Rest periods may optionally be provided between the treatment sessions, for example each of which has a duration of several seconds or several minutes. For example, control circuitry 34 may be configured to apply the respective currents during a portion of each treatment session, the portion having a duration greater than half of the total duration of the treatment session. For some applications, the respective currents are not applied for a period that is at least an hour. For some applications, control circuitry 34 is configured to apply the respective currents with a constant current (i.e., non-pulsed current) when applied.

Optionally, control circuitry 34 is activated to apply the respective currents only when the subject is sleeping, such as to inhibit any sensations that may be associated with application of the respective currents. For example, control circuitry 34 may be activated to use one or more of the electrodes as EEG electrodes to detect sleep. For some applications, power for activating and/or charging control circuitry 34 is transmitted from a wireless energy transmitter in a hat or from a wireless energy transmitter in, under, or above a mattress. For some applications, control circuitry 34 is activated to apply the respective currents according to a pre-selected schedule, such as a duty cycle, such as for a few hours per day. For example, control circuitry 34 may be configured to be controlled and/or powered by an extracorporeal control circuitry, such as a control circuitry comprising a wireless transmitter, disposed in and/or in the vicinity of the subject's bed. For some applications, one or more rest periods during which the respective currents are not applied are provided in the pre-selected schedule.

For some applications, system 20 comprises a housing, which contains control circuitry 34. For some applications, the housing is implantable, such as subcutaneously; for example, the housing may be similar to conventional pacemaker housings ("cans"). For some applications, the housing comprises first, second, and third lead interfaces, for electrical and mechanical coupling with central lead 70 and left and right peripheral leads 72A and 72B. For example, the first, the second, and the third lead interfaces may comprise first, second, and third ports, into which corresponding connectors of the leads are inserted. Alternatively, the leads may have hardwired connections with the lead interfaces. The first, the second, and the third lead interfaces are also electrically coupled with control circuitry 34.

Typically, the lead interfaces are physically arranged such that the second lead interface is between the first and the third lead interfaces on the housing. Typically, control circuitry 34 is configured to apply the respective currents through the second lead interface to central lead 70 such that central electrodes 30 are cathodes, and to apply the respective currents through the first and the third lead interfaces such that peripheral electrodes 32 (e.g., left and right peripheral electrodes 32A and 32B) are anodes.

Alternatively, for some applications, the housing comprises only two lead interfaces, and the left and the right peripheral leads are electrically coupled to each other so as define a single, joint connector, which is couplable to one of the lead interfaces of the housing.

Reference is made to FIGS. 1A-3. For any of the applications described herein, system 20 may comprise:
- a single central electrode 30, rather than a plurality of central electrodes 30,
- a single left lateral treatment electrode 32A, rather than a plurality of left peripheral electrodes 32A, and/or
- a single right lateral treatment electrode 32B, rather than a plurality of right peripheral electrodes 32B.

For some of these applications, any of these single electrodes comprises an elongate electrode having a length of at least 10 cm, no more than 40 cm (e.g., no more than 30 cm), and/or 10-40 cm (e.g., 10-30 cm); for example, the elongate electrode may comprise an electrically-non-insulated wire.

Although control circuitry 34 has generally been described hereinabove as being configured to configure central electrodes 30 as cathodes and peripheral electrodes 32 (e.g., left peripheral electrodes 32A and right peripheral electrodes 32B) as anodes, control circuitry 34 may alternatively be configured to configure electrodes 30 as anodes and peripheral electrodes 32 (e.g., left peripheral electrodes 32A and right peripheral electrodes 32B) as cathodes. This electrical polarity treats the subject by clearing the substance (e.g., amyloid beta, tau protein, and/or metal ions) from brain parenchyma 66 to superior sagittal sinus 40, typically via arachnoid granulations and/or villi.

In an embodiment, techniques and apparatus described in one or more of the following applications, which are assigned to the assignee of the present application and are incorporated herein by reference, are combined with techniques and apparatus described herein:

U.S. Pat. No. 9,731,122 to Gross;
U.S. Pat. No. 9,616,221 to Gross;
PCT Publication WO 2017/006327 to Gross;
U.S. Pat. No. 9,724,515 to Fostick et al.;
PCT Publication WO 2017/072769 to Fostick et al.;
U.S. Pat. No. 10,569,086 to Fostick et al.;
U.S. Pat. No. 10,758,722 to Gross et al.;
U.S. Pat. No. 11,202,905 to Tendler et al.;
PCT Publication WO 2019/175879 to Tendler et al.;
U.S. Pat. No. 10,881,858 to Gross et al.; and
PCT Publication WO 2021/053676 to Gross et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method comprising:
disposing central electrodes outside and in electrical contact with a skull of a head of a subject identified as at risk of or suffering from Alzheimer's disease, within one cm of a sagittal midplane of the skull;
disposing peripheral electrodes outside and in electrical contact with the skull, superior to an orbitomeatal plane of the skull and inferior to a first plane midway between the orbitomeatal plane and a cranial vertex of the skull, the first plane parallel to the orbitomeatal plane; and
treating the subject by clearing a substance from brain parenchyma to a subarachnoid space, the substance selected from the group consisting of: amyloid beta, tau protein, and metal ions, by activating control circuitry to:
apply respective currents between one or more of the central electrodes and two or more of the peripheral electrodes, and
configure the central electrodes as cathodes and the peripheral electrodes as anodes.

2. The method according to claim 1, wherein the substance is the amyloid beta, and wherein clearing the substance comprises clearing the amyloid beta from the brain parenchyma to the subarachnoid space.

3. The method according to claim 1, wherein the substance is the tau protein, and wherein clearing the substance comprises clearing the tau protein from the brain parenchyma to the subarachnoid space.

4. The method according to claim 1, wherein disposing the peripheral electrodes comprises disposing the peripheral electrodes inferior to a second plane located at a distance from the orbitomeatal plane equal to 40% of a distance between the orbitomeatal plane and the cranial vertex, the second plane parallel to the orbitomeatal plane.

5. The method according to claim 1, wherein disposing the peripheral electrodes comprises disposing the peripheral electrodes superior to a third plane located at a distance from the orbitomeatal plane equal to 5% of a distance between the orbitomeatal plane and the cranial vertex, the third plane parallel to the orbitomeatal plane.

6. The method according to claim 5, wherein the third plane is located at a distance from the orbitomeatal plane equal to 10% of the distance between the orbitomeatal plane and the cranial vertex.

7. The method according to claim 1, wherein disposing the central electrodes and the peripheral electrodes comprises disposing all of the central electrodes superior to all of the peripheral electrodes.

8. The method according to claim 1, wherein disposing the central electrodes and the peripheral electrodes comprises disposing at least 90% of the central electrodes superior to all of the peripheral electrodes.

9. The method according to claim 1, wherein disposing the central electrodes and the peripheral electrodes comprises disposing the central electrodes at respective distances from respective closest ones of the peripheral electrodes, the distances measured along an external surface of the head, each of the distances at least 4 cm.

10. The method according to claim 1, wherein disposing the central electrodes and the peripheral electrodes comprises disposing the central electrodes at respective distances from respective closest ones of the peripheral electrodes, the distances measured along an external surface of the head, at least 90% of the distances at least 4 cm.

11. The method according to claim 1, wherein disposing the peripheral electrodes comprises disposing an anteriormost one of the peripheral electrodes within a distance from the sagittal midplane, the distance measured along an external surface of the head, the distance no more than 5 cm.

12. The method according to claim 1, wherein disposing the peripheral electrodes comprises disposing a posteriormost one of the peripheral electrodes within a distance from the sagittal midplane, the distance measured along an external surface of the head, the distance no more than 5 cm.

13. The method according to claim 1,
wherein the peripheral electrodes include left peripheral electrodes and right peripheral electrodes,
wherein disposing the peripheral electrodes comprises disposing the left peripheral electrodes and right peripheral electrodes outside and in electrical contact with the skull, left and right of the sagittal midplane, respectively, superior to the orbitomeatal plane and inferior to the first plane, and
wherein activating the control circuitry comprises activating the control circuitry to:
apply the respective currents (a) between the one or more of the central electrodes and one or more of the left peripheral electrodes and (b) between one or more of the central electrodes and one or more of the right peripheral electrodes, and configure the central electrodes as the cathodes, the left peripheral electrodes as anodes, and the right peripheral electrodes as anodes.

14. The method according to claim 13, wherein disposing the left peripheral electrodes and the right peripheral electrodes comprises disposing a left anterior-most one of the left peripheral electrodes and a right anterior-most one of the right peripheral electrodes, respectively, within respective distances from the sagittal midplane, the distances measured along an external surface of the head, each of the distances no more than 5 cm.

15. The method according to claim 13, wherein disposing the left peripheral electrodes and the right peripheral electrodes comprises disposing a left posterior-most one of the left peripheral electrodes and a right posterior-most one of the right peripheral electrodes, respectively, within respective distances from the sagittal midplane, the distances measured along an external surface of the head, each of the distances no more than 5 cm.

16. The method according to claim 13, wherein disposing the left peripheral electrodes and the right peripheral electrodes comprises disposing at least five left peripheral electrodes and at least five right peripheral electrodes, respectively.

17. The method according to claim 13, wherein activating the control circuitry to apply the respective currents (a) between the one or more of the central electrodes and the one or more of the left peripheral electrodes and (b) between the one or more of the central electrodes and the one or more of the right peripheral electrodes comprises activating the control circuitry to apply:
 a first current between a first one of the central electrodes and a first one of the left peripheral electrodes,
 a second current between the first one of the central electrodes and a first one of the right peripheral electrodes,
 a third current between a second one of the central electrodes and a second one of the left peripheral electrodes, and
 a fourth current between the second one of the central electrodes and a second one of the right peripheral electrodes.

18. The method according to claim 1,
 wherein the peripheral electrodes are left peripheral electrodes,
 wherein disposing the peripheral electrodes comprises disposing the left peripheral electrodes outside and in electrical contact with the skull, left of the sagittal midplane, superior to the orbitomeatal plane and inferior to the first plane, and
 wherein activating the control circuitry comprises activating the control circuitry to:
  apply the respective currents between the one or more of the central electrodes and two or more of the left peripheral electrodes, and
  configure the central electrodes as the cathodes and the left peripheral electrodes as the anodes.

19. The method according to claim 18, wherein all of the peripheral electrodes are the left peripheral electrodes, and wherein the method does not comprise disposing any of the peripheral electrodes more than one cm right of the sagittal midplane of the skull.

20. The method according to claim 18, wherein disposing the left peripheral electrodes comprises disposing the left peripheral electrodes in a first series and a second series, the left peripheral electrodes of the first series located at least a distance superior to the left peripheral electrodes of the second series, the distance measured along an external surface of the head, and the distance at least 3 cm.

21. The method according to claim 1, wherein activating the control circuitry to apply the respective currents comprises activating the control circuitry to set the respective currents to have respective amplitudes of 1-5 milliamps.

22. The method according to claim 1, wherein activating the control circuitry to apply the respective currents comprises activating the control circuitry to set each of the respective currents to the lesser of (a) a predefined maximum current and (b) a current that results from application of a predefined maximum voltage.

23. The method according to claim 22, wherein the predefined maximum voltage is 2-15 V.

24. The method according to claim 1, wherein disposing the peripheral electrodes comprises disposing peripheral electrodes outside the head.

25. The method according to claim 24, wherein disposing the peripheral electrodes comprises disposing the peripheral electrodes on an external surface of the head.

26. The method according to claim 1, wherein disposing the peripheral electrodes comprises implanting the peripheral electrodes under skin of the head.

27. The method according to claim 1, wherein disposing the central electrodes comprises disposing the central electrodes outside the head.

28. The method according to claim 27, wherein disposing the central electrodes comprises disposing the central electrodes on an external surface of the head.

29. The method according to claim 1, wherein disposing the central electrodes comprises implanting the central electrodes under skin of the head.

30. The method according to claim 1, wherein disposing the central electrodes comprises disposing at least five central electrodes.

31. The method according to claim 1, wherein disposing the peripheral electrodes comprises disposing at least five peripheral electrodes.

32. The method according to claim 1, wherein activating the control circuitry comprises activating the control circuitry to apply the respective currents to as respective DC currents.

* * * * *